(12) United States Patent
Matsumoto (10) Patent No.: US 8,475,043 B2
(45) Date of Patent: Jul. 2, 2013

(54) RADIATION IMAGING APPARATUS AND PROCESSING METHOD THEREFOR

(75) Inventor: Kazuhiro Matsumoto, Saitama (JP)

(73) Assignee: Canon Kabushiki Kaisha, Tokyo (JP)

( * ) Notice: Subject to any disclaimer, the term of this patent is extended or adjusted under 35 U.S.C. 154(b) by 649 days.

(21) Appl. No.: 12/699,526

(22) Filed: Feb. 3, 2010

(65) Prior Publication Data

US 2010/0213378 A1 Aug. 26, 2010

(30) Foreign Application Priority Data

Feb. 24, 2009 (JP) ................................. 2009-041300

(51) Int. Cl.
*A61B 6/00* (2006.01)
(52) U.S. Cl.
USPC ............................ 378/205; 378/197; 378/207
(58) Field of Classification Search
USPC ............................. 378/98, 197, 207, 62, 205
See application file for complete search history.

(56) References Cited

U.S. PATENT DOCUMENTS

| 6,412,978 B1 | 7/2002 | Watanabe et al. ............. 378/197 |
| 2004/0131154 A1 | 7/2004 | Watanabe et al. ............ 378/98.8 |

FOREIGN PATENT DOCUMENTS

| JP | 56-093300 | 7/1981 |
| JP | 58-085687 | 5/1983 |
| JP | 10-071141 | 3/1998 |
| JP | 2005-027806 | 2/2005 |
| JP | 2008-142236 | 6/2008 |

OTHER PUBLICATIONS

Translation for JP 2008-142236 published on Jun. 26, 2008.*
Translation for JP 10-071141 published on Mar. 17, 1998.*
European Search Report in European Patent Application No. EP 10151948.6. Dated Jun. 22, 2010.

* cited by examiner

*Primary Examiner* — Glen Kao
(74) *Attorney, Agent, or Firm* — Fitzpatrick, Cella, Harper & Scinto (57) ABSTRACT

A radiation imaging apparatus comprises a radiation generator configured to irradiate an object with radiation, a radiation detector configured to detect radiation transmitted through the object, a detector configured to detect movement or rotation or both of the radiation generator and the radiation detector relative to the object, and a controller configured to change the size of the irradiated region of the object based on a detection result.

9 Claims, 9 Drawing Sheets

OUTSIDE VIEW OF C-ARM

DISPLAY ON MONITOR

FIG. 9

RADIATION IMAGING APPARATUS AND PROCESSING METHOD THEREFOR

BACKGROUND OF THE INVENTION

1. Field of the Invention

The present invention relates to a radiation imaging apparatus and a processing method therefor.

2. Description of the Related Art

A radiation imaging apparatus is known, which obtains a radiographic image based on the detection of radiation (e.g., X-rays) transmitted through an object. For example, the radiation imaging apparatus obtains images of an imaging target such as the alimentary canal with radiation. Radiation imaging apparatuses are widely used in routine health check-ups and the like as well as examinations at the time of medical treatment.

Radiation imaging apparatuses are available in various forms. As disclosed in, for example, Japanese Patent Laid-Open No. 2005-27806, there is available an apparatus which fluoroscopes and images an object, with the object placed on the top panel of a bed that is positioned between an X-ray generator and an X-ray detector mounted on the two ends of a supporting member called a C-arm. The X-rays emitted from the X-ray generator pass through the object and strike the X-ray detector. The X-ray detector converts the X-rays transmitted through this object into an optical signal. Executing this operation under predetermined X-ray irradiation conditions can allow display of a fluoroscopic image of an object on a monitor in real time.

In the above X-ray imaging apparatus, the operation steps associated with fluoroscopy and imaging performed by an operator are roughly classified into 1) positioning while performing fluoroscopy, 2) diagnosis in fluoroscopic state (check on an imaging target), and 3) imaging of a positioned target.

In portion 1), positioning while performing fluoroscopy, positioning is performed to display an imaging target in a desired size at a proper position (e.g., a middle position) on a monitor. In such positioning, the operator moves the X-ray generator, the X-ray detector, and the top panel. That is, since the operator moves them during positioning, the fluoroscopic image (observed image) displayed on the monitor moves.

In contrast to this, in portion 2), diagnosis in fluoroscopic state (checking on the imaging target), the operator does not perform a positioning operation, and the observed image on the monitor is therefore fixed. Thereafter, when the operator visually checks the imaging target, the apparatus executes portion 3), imaging of the positioned target, under predetermined X-ray irradiation conditions. As described above, when performing X-ray imaging, operation steps 1) to 3) are repeated.

In general, in a medical situation using X-rays, important management and study items include: how to shorten the time required for fluoroscopy and imaging and how to reduce the X-ray exposure dose for the subject (herein, the patient may sometimes be referred to as the "subject", and the particular portion of the body being studied may is sometimes termed the "object").

In, for example, the positioning while performing fluoroscopy, if a region of an image displayed on the monitor is suitable for the positioning operation, the operator can easily find the imaging target, and hence it is possible to shorten the time required for positioning. In addition, if the apparatus is configured not to image unnecessary regions which do not contribute to the positioning operation for the imaging target, it is possible to reduce the X-ray exposure dose delivered to the patient.

SUMMARY OF THE INVENTION

The present invention provides a technique of shortening the time required for a positioning operation by improving operability at the time of the positioning operation.

According to a first aspect of the present invention, there is provided a radiation imaging apparatus comprising a radiation generator arranged to irradiate an object with radiation, a radiation detector arranged to detect radiation transmitted through the object, a detector arranged to detect movement or rotation (or both) of the radiation generator and the radiation detector relative to the object, and a controller arranged to change the size of an irradiation region of the object based on the output of the detector.

According to a second aspect of the present invention, there is provided a processing method in a radiation imaging apparatus which obtains a radiographic image, the method comprising causing a radiation generator to irradiate an object with radiation, causing a radiation detector to detect radiation transmitted through the object, detecting movement or rotation (or both) of the radiation generator and the radiation detector relative to the object, and changing the size of the irradiated region of the object based on the detection result.

Further features of the present invention will be apparent from the following description of exemplary embodiments with reference to the attached drawings.

DESCRIPTION OF THE EMBODIMENTS

An exemplary embodiment of the present invention will now be described in detail with reference to the drawings. It should be noted that the relative arrangement of the components, the numerical expressions and numerical values set forth in these embodiments do not limit the scope of the present invention unless it is specifically stated otherwise.

Note that the following embodiment will exemplify a case in which X-rays are used as the radiation. However, the "radiation" to be used is not limited to X-rays, and it is possible to use electromagnetic waves more generally, and beams of α- or β-particles, γ-rays, and the like may also be considered for use.

In addition, the following embodiment will be described by taking an X-ray imaging apparatus equipped with a C-arm as an example of a radiation imaging apparatus. This X-ray imaging apparatus performs imaging while moving or rotating an imaging system formed by coupling an X-ray generator to an X-ray detector. Note that the present invention is not limited to this type of X-ray imaging apparatus, and can be applied to, for example, a table-type X-ray imaging apparatus (an RF imaging apparatus).

Figure 1:
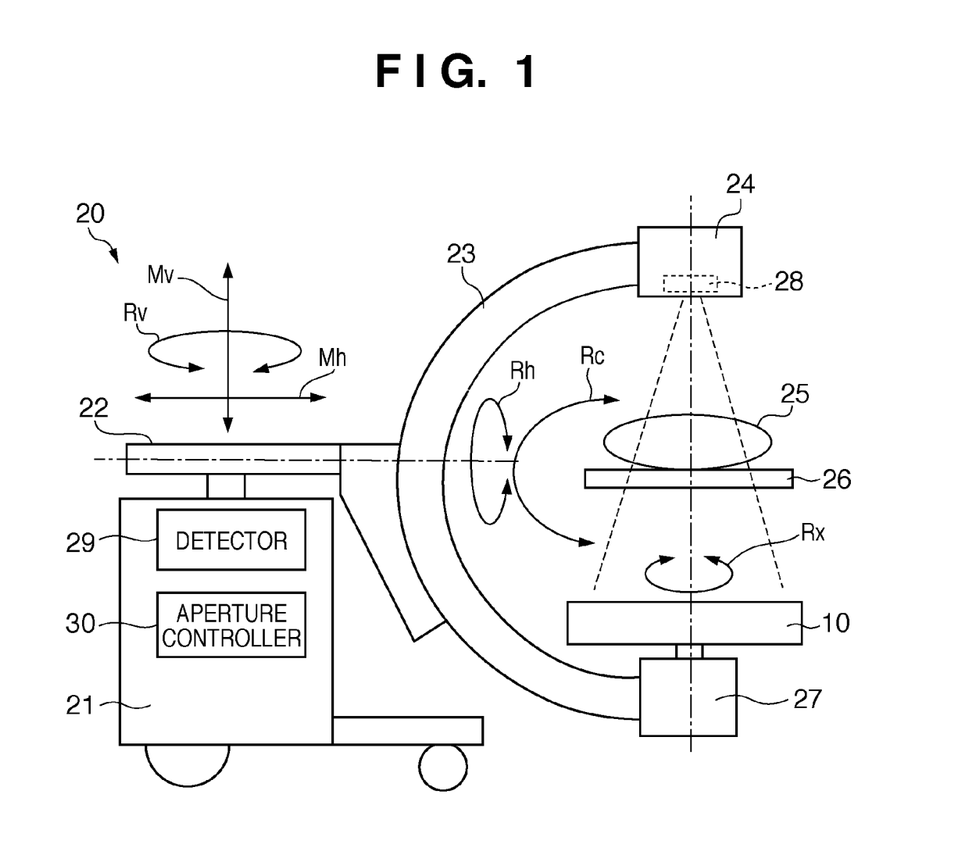
FIG. 1 is a view showing an example of the arrangement of an X-ray imaging apparatus 20 according to an embodiment of the present invention.

FIG. 1 is a view showing an example of the arrangement of an X-ray imaging apparatus 20 according to an embodiment of the present invention.

The X-ray imaging apparatus 20 includes one or a plurality of computers. The computer includes, for example, a main controller such as a CPU and storage units such as a ROM (Read Only Memory) and a RAM (Random Access Memory). The computer may include a communication unit such as a network card and input/output units such as a keyboard, a mouse, a display, and a touch panel. Note that these constituent elements are connected to each other via buses, and are controlled by causing the main controller to execute the programs stored in the storage units.

In this case, the X-ray imaging apparatus 20 includes a main body unit 21, a horizontal shaft 22, and a C-arm 23. The horizontal shaft 22 is supported on the main body unit 21 and moves up and down. The C-arm 23 is provided on the distal end of the horizontal shaft 22, and is formed from a C-shaped arm member. The horizontal shaft 22 and the C-arm 23 rotate in the directions indicated by arrows Rc, Rh, and Rv and move in the directions indicated by arrows Mh and Mv in FIG. 1.

An X-ray generator 24 and an X-ray detector 10 are provided on the two ends of the C-arm 23 so as to face each other. The C-arm 23 supports the X-ray generator 24 and the X-ray detector 10 so as to keep their distance constant. A movable mechanism (not shown) positions the X-ray generator 24 and the X-ray detector 10 at arbitrary positions and angles relative to an object 25.

The X-ray generator 24 functions as a radiation generator and irradiates (exposes) an object (e.g., a portion of a patient's body) with radiation (X-rays). The X-ray detector 10 functions as a radiation detector, and detects X-rays transmitted through an object. The object 25 is supported on a top panel 26 functioning as an object supporting unit. The top panel 26 is provided between the X-ray generator 24 and the X-ray detector 10.

The effective imaging region of the X-ray detector 10 is rectangular rather than circular. It is therefore necessary, depending on the target to be imaged, to adjust the positional relationship between the object and the X-ray detector 10. The movable mechanism of the X-ray imaging apparatus 20 generally performs such positional relationship adjustment (positioning). In order to improve operability, however, it is preferable to allow the X-ray detector 10 to pivot within the X-ray irradiation plane. For this reason, this embodiment provides the X-ray imaging apparatus 20 with a mechanism to rotate the X-ray detector 10, in the direction indicated by arrow Rx, about an axis 27 (i.e., an X-ray irradiation axis) connecting the middle of the effective imaging region and the X-ray generator 24 as a rotation center.

The X-ray generator 24 includes an aperture unit 28. The aperture unit 28 functions as an aperture mechanism to adjust the amount of X-rays (radiation dose). This mechanism changes the X-ray irradiated region (especially, the size of the irradiated region). The aperture unit 28 includes a shield (for example, formed from a heavy metal such as lead which has a high X-ray shielding ratio) to adjust the amount of X-rays delivered to the object (radiation dose). This allows the X-ray generator 24 to irradiate the object 25 with X-rays in an optimal shape in accordance with the imaging target. The aperture unit 28 may have an arrangement in which two shielding mechanisms to change the opening width by using two shields are arranged orthogonally (rectangular arrangement). Alternatively, the aperture unit 28 can have a circular arrangement, a polygonal arrangement, or the like.

In addition, the main body unit 21 includes, as functional arrangements, for example, a detector 29 and an aperture controller 30. The detector 29 detects information concerning the rotation and movement of the horizontal shaft 22 (e.g., a moving direction, a moving amount, and a moving speed). That is, the detector 29 detects the movement of the horizontal shaft 22 in the Mh direction and Mv direction and the rotation of the horizontal shaft 22 in the Rv direction. As the detector 29, for example, a linear encoder can be used. The aperture controller 30 controls the operation (stopping down) of the aperture unit 28.

In an X-ray imaging apparatus 20 having this arrangement, the operator performs a positioning operation to image a desired imaging target 31 of the object 25 while observing the obtained image displayed on the monitor (not shown).

Figure 2:
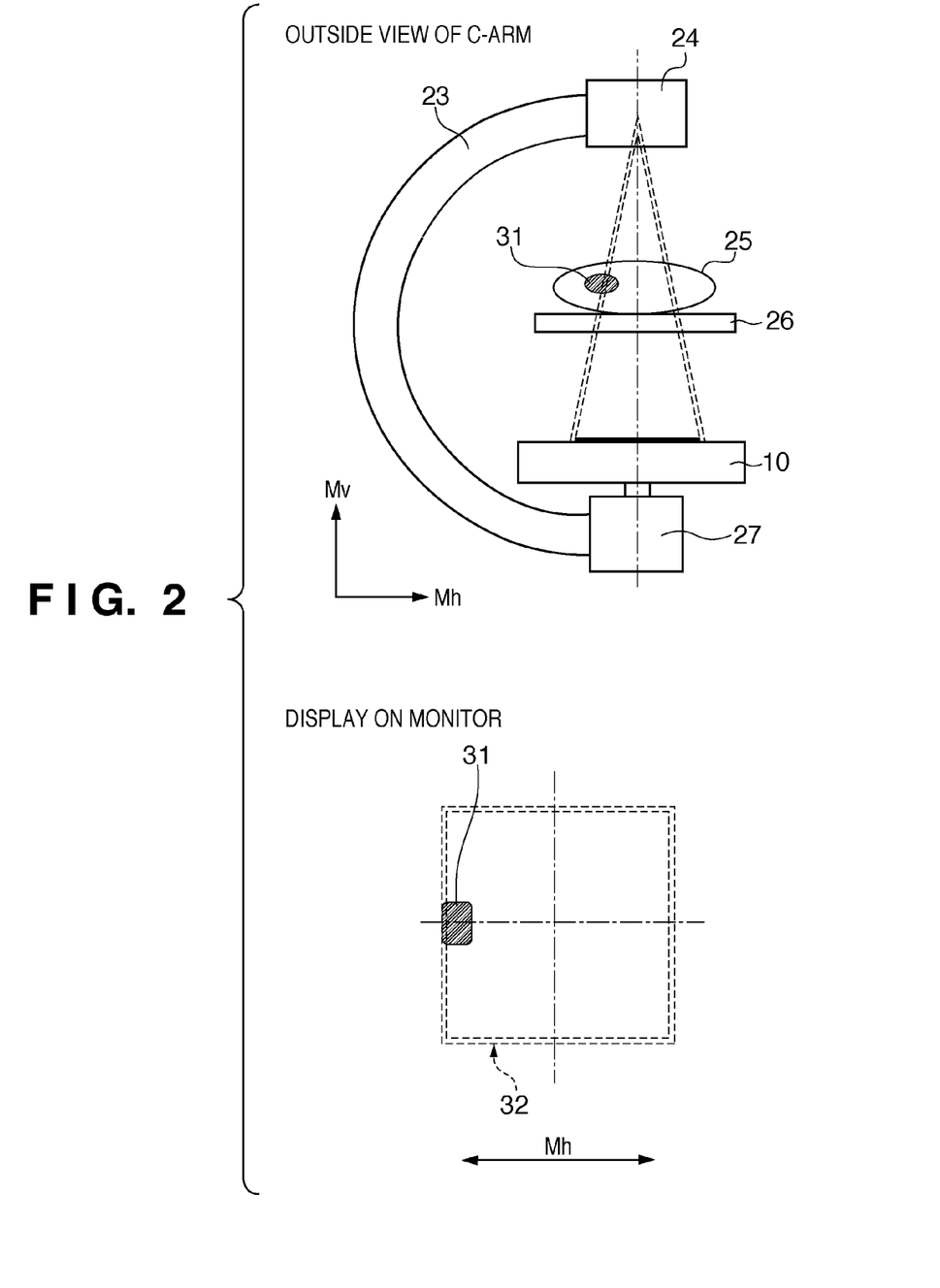
FIG. 2 is a view showing an example of the positional relationship between a C-arm 23 and a desired imaging target 31 and of the display form of a monitor.
Figure 3:
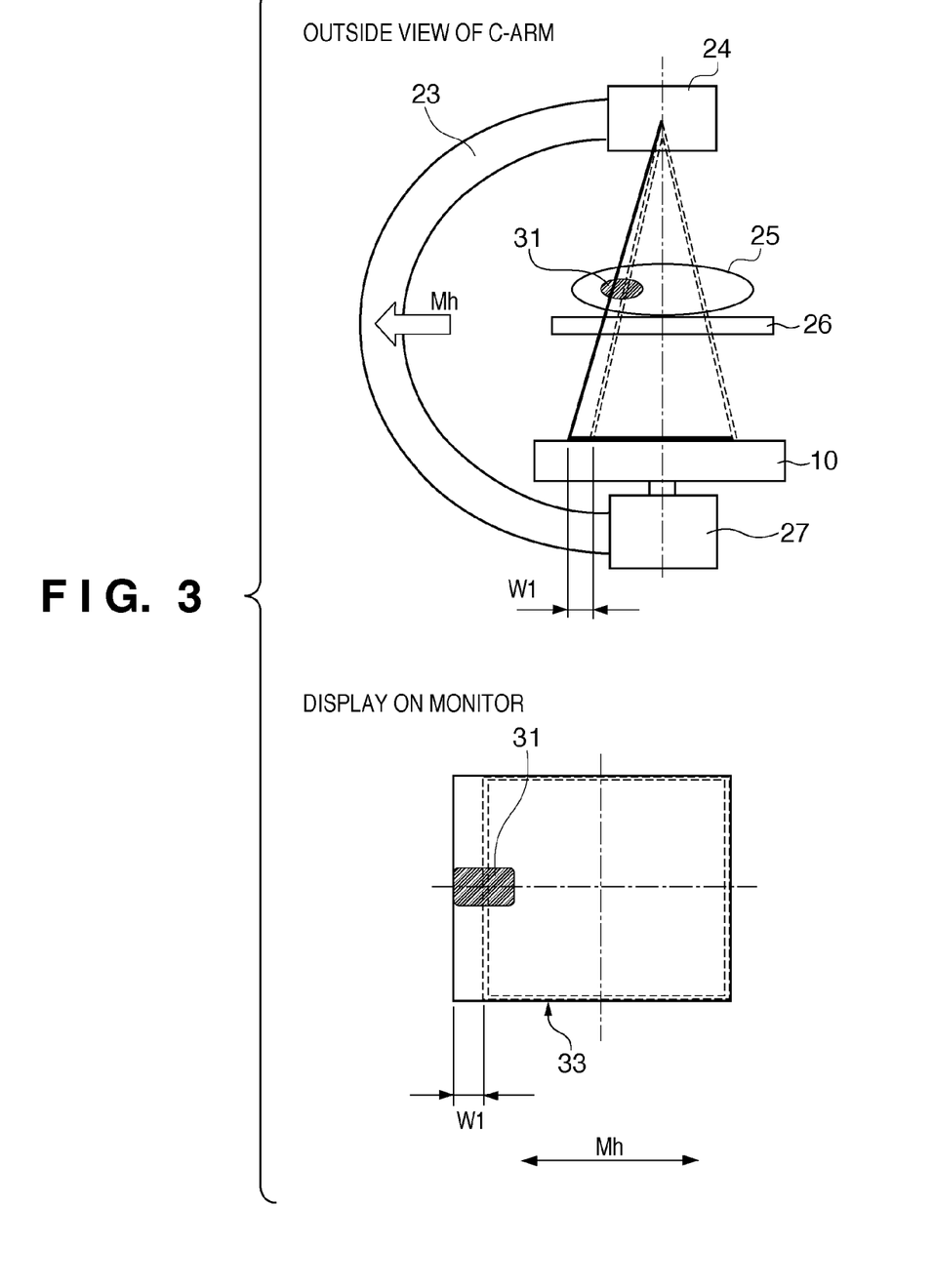
FIG. 3 is a view showing an example of the positional relationship between the C-arm 23 and the desired imaging target 31 and of the display form of the monitor.

Imaging control processing at the time of a positioning operation according to this embodiment will be described below. Assume that imaging is performed while the desired imaging target 31 of the object 25 and the X-ray imaging apparatus 20 have the positional relationship shown in FIG. 2. In this case, since only the right portion of the desired imaging target 31 is irradiated with X-rays, the monitor displays only an image of the right portion of the desired imaging target 31, as shown in FIG. 2. When imaging the left portion of the desired imaging target 31, the operator moves the C-arm 23 in the Mh direction (more specifically, the direction to move away from the object 25). With this operation, the X-ray generator 24 and the X-ray detector 10 move relative to the object. During the movement of the C-arm 23, as shown in FIG. 3, the irradiated region on the left end is enlarged in the leftward direction, and the monitor displays an image with the desired imaging target 31 being imaged in a wider range. That is, this embodiment enlarges the irradiated region on the moving direction side, referring to the moving direction of the irradiated region, which moves in accordance with the moving direction of the C-arm 23.

Figure 4:
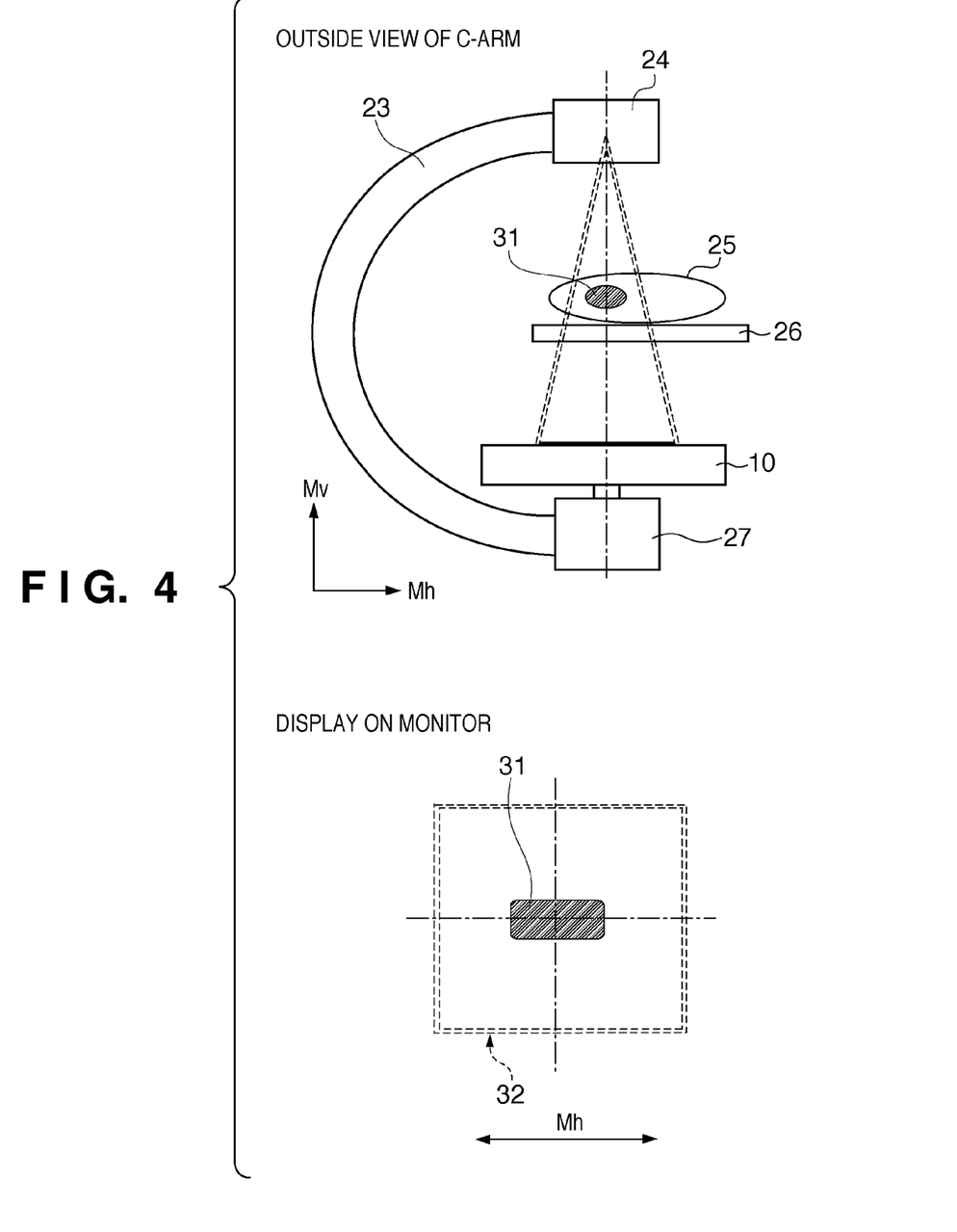
FIG. 4 is a view showing an example of the positional relationship between the C-arm 23 and the desired imaging target 31 and of the display form of the monitor.

Thereafter, the operator moves the C-arm 23 until the desired imaging target 31 is positioned on the middle portion of the monitor, that is, on the X-ray irradiation axis 27. When the positioning operation is complete and the C-arm 23 stops, the irradiated region is restored to the initial state as shown in FIG. 4, that is, the irradiated region has the same size as that shown in FIG. 2. As a consequence, the desired imaging target 31 is displayed in the middle of the monitor.

Figure 5:
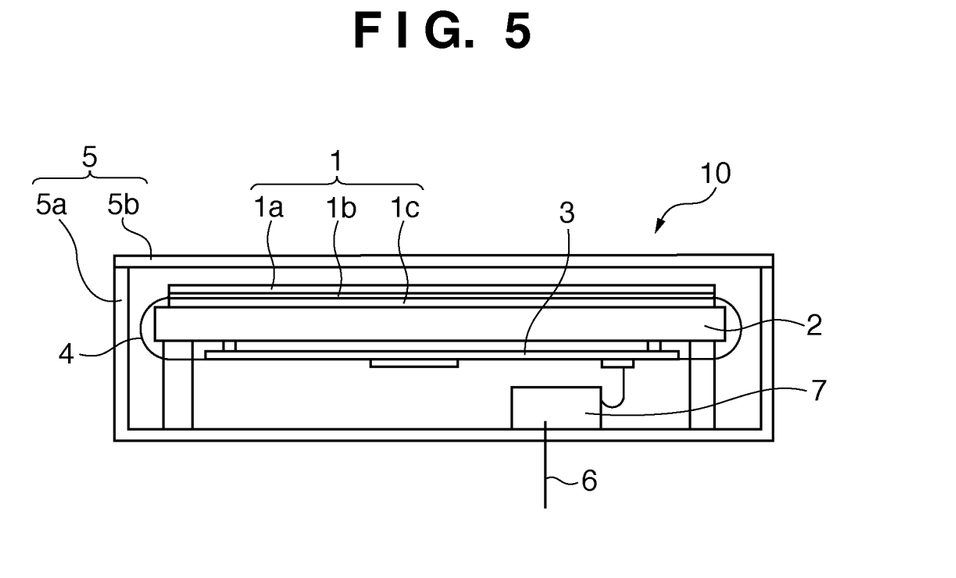
FIG. 5 is a view showing an example of the sectional arrangement of the interior of an X-ray detector 10 shown in FIG. 1.

An example of the sectional arrangement of the interior of the X-ray detector 10 shown in FIG. 1 will be described with reference to FIG. 5.

Detection panel 1 is a panel to detect X-rays transmitted through an object. The detection panel 1 includes a fluorescent screen 1a, photoelectric conversion elements 1b, and a substrate 1c. As the substrate 1c, for example, a glass plate can be used. The photoelectric conversion elements 1b are two-dimensionally (or one-dimensionally) arrayed on such a glass substrate. A read circuit to read out photoelectrically converted electrical signals, a driving circuit for selecting elements to be read, and the like are connected to an end portion of the detection panel 1. The detection panel 1 has a rectangular shape, on which the read circuit and the driving circuit are respectively arranged on orthogonal sides.

As the fluorescent screen 1a, for example, a resin plate coated with a phosphor made of a metallic compound is used. The fluorescent screen 1a is formed integrally with the substrate 1c, and is fixed as the detection panel 1 on a base 2 made of a metal. An electric substrate 3 is arranged on the rear side of the base 2. The electric substrate 3 generates an X-ray image (radiographic image) based on the electrical signal obtained from the detection panel 1. Note that the electric substrate 3 is connected to the detection panel 1 via a flexible circuit board 4.

The base 2 is fixed to a housing 5a. The X-ray detector 10 is hermetically sealed by the housing 5a and a housing lid 5b made of a material having high X-ray transmittance. The X-ray detector 10 is connected to an external controller (not shown) via a cable 6 and a relay electric circuit unit 7. With this arrangement, the X-ray detector 10, for example, supplies power and transfers signals.

The X-ray detector 10 obtains an X-ray image based on the X-rays transmitted through an object, as described above. When the X-rays transmitted through the object strike the X-ray detector 10, the phosphor emits light, and the two-dimensionally arrayed photoelectric conversion elements 1b convert the light into an electrical signal. This signal is then transferred as electrical image information via the cable 6. With this operation, the operator can observe the obtained image on the monitor in real time.

Figure 6:
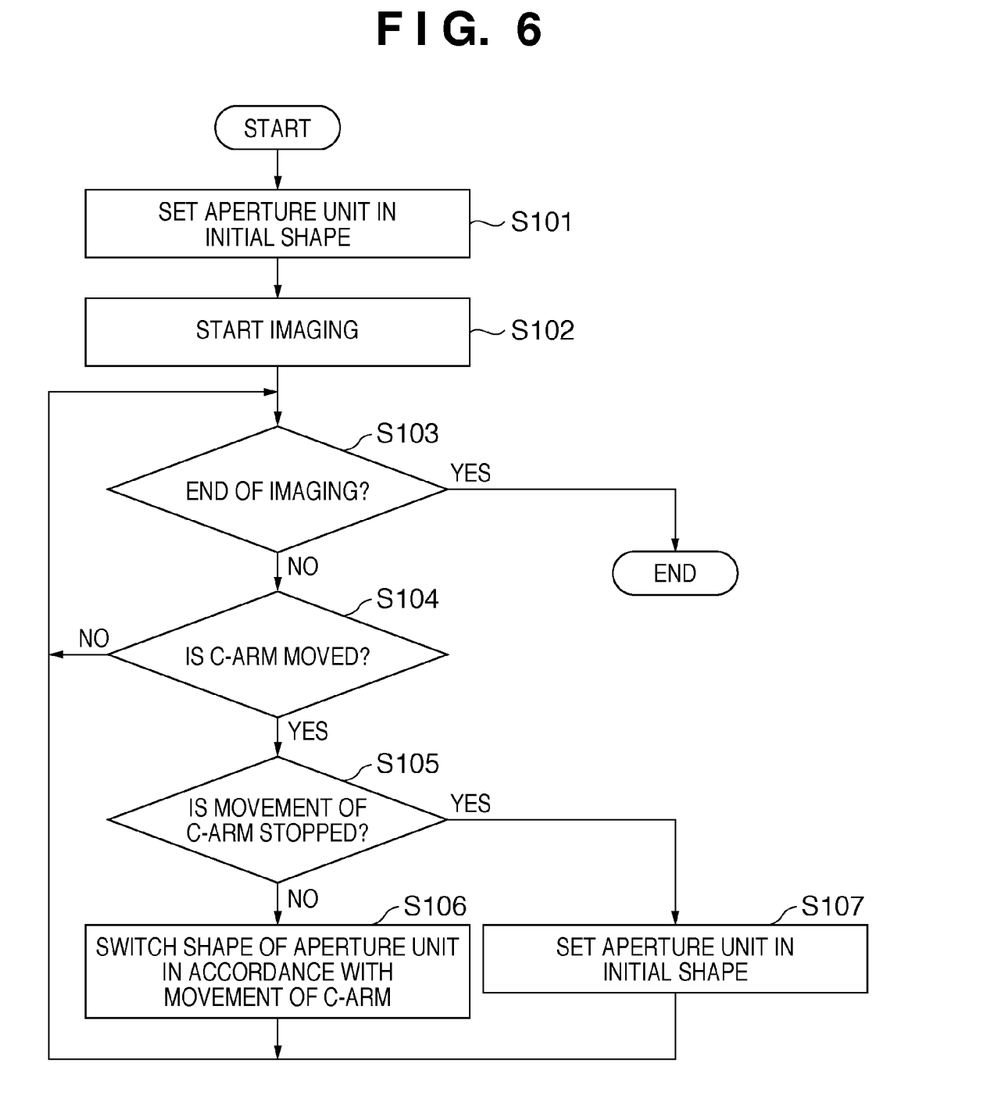
FIG. 6 is a flowchart showing an example of the imaging operation of the X-ray imaging apparatus 20 shown in FIG. 1.

An example of the imaging operation of the X-ray imaging apparatus 20 shown in FIG. 1 will be described next with reference to FIG. 6.

When imaging processing starts, the X-ray imaging apparatus 20 causes an aperture controller 30 to set the aperture of the aperture unit 28 in the initial state (initial shape) (S101). The initial shape of the aperture is determined in advance in accordance with the size of the desired imaging target 31 or the like.

Subsequently, the X-ray imaging apparatus 20 starts imaging the object 25 (S102). More specifically, the X-ray generator 24 irradiates an X-ray object (e.g., a human body) with X-rays. The X-ray detector 10 obtains an X-ray image based on the X-rays transmitted through the object. With this operation, as shown in FIG. 2, the monitor displays an image obtained while the aperture of the aperture unit 28 is in the initial shape.

If the operator issues an instruction (or if one is issued automatically) to finish imaging (YES in step S103), this imaging processing ends. If no instruction to finish imaging is issued (NO in step S103), the X-ray imaging apparatus 20 causes the detector 29 to detect information concerning the rotation or movement of the horizontal shaft 22, thereby intermittently monitoring the movement of the C-arm during this imaging operation.

As a result, if there is no change in detection result (NO in step S104), the X-ray imaging apparatus 20 maintains the current imaging state. On the other hand, if movement of the C-arm 23 is detected (YES in step S104), the X-ray imaging apparatus 20 determines that the C-arm 23 should be stopped. The X-ray imaging apparatus 20 performs this determination based on the detection result obtained by the detector 29.

If the C-arm 23 is not at rest, that is, if it is moving (NO in step S105), the X-ray imaging apparatus 20 causes the aperture controller 30 to change the shape of the aperture unit 28 in accordance with the movement of the C-arm 23 (i.e., the detection result obtained by the detector 29) (S106). That is, the aperture controller 30 controls the movement of the shield of the aperture unit 28 in accordance with the movement of the C-arm 23 to switch the shape of the aperture to a shape other than the initial shape. If, for example, the C-arm 23 is moving in the direction away from the object 25 in the Mh direction (i.e., to the left side), the aperture controller 30 enlarges the irradiated region on the left end in the leftward direction by a width W1, as shown in FIG. 3. With this operation, the left side of the desired imaging target 31, which has not been imaged, is imaged in a wider range. The monitor then displays the obtained image as an image region 33. The aperture controller 30 switches the shape of the aperture unit 28 in step S105 every time the C-arm 23 moves. If, for example, the moving direction of the C-arm 23 changes to the opposite direction, the aperture controller 30 restores the shape of the X-ray irradiated region, which has been enlarged in the leftward direction by the width W1, to the initial shape, and enlarges the irradiated region on the right end in the rightward direction by W1.

Upon detecting that the C-arm 23 has stopped in step S105, the X-ray imaging apparatus 20 causes the aperture controller 30 to set (restore) the aperture of the aperture unit 28 to the initial state (initial shape) (S107). Thereafter, the X-ray imaging apparatus 20 returns to the processing in step S103 and repeats the above processing until the imaging operation is complete. For example, the operator stops the movement of the C-arm 23 when the desired imaging target 31 is positioned at the middle portion of the monitor. With this operation, the enlarged irradiated region returns to its initial state. At this time, as shown in FIG. 4, the desired imaging target 31 is displayed near the middle of an initial image region 32.

As described above, according to this embodiment, an irradiated region is enlarged in accordance with positioning operation by the operator. This improves operability during the positioning operation and makes it easy to find a desired imaging target, thereby shortening the time required for the positioning.

The preferred embodiment of the present invention has been described above. Obviously, however, the present invention is not limited to this embodiment, and can be variously modified and changed within the spirit and scope of the invention.

Figure 7:
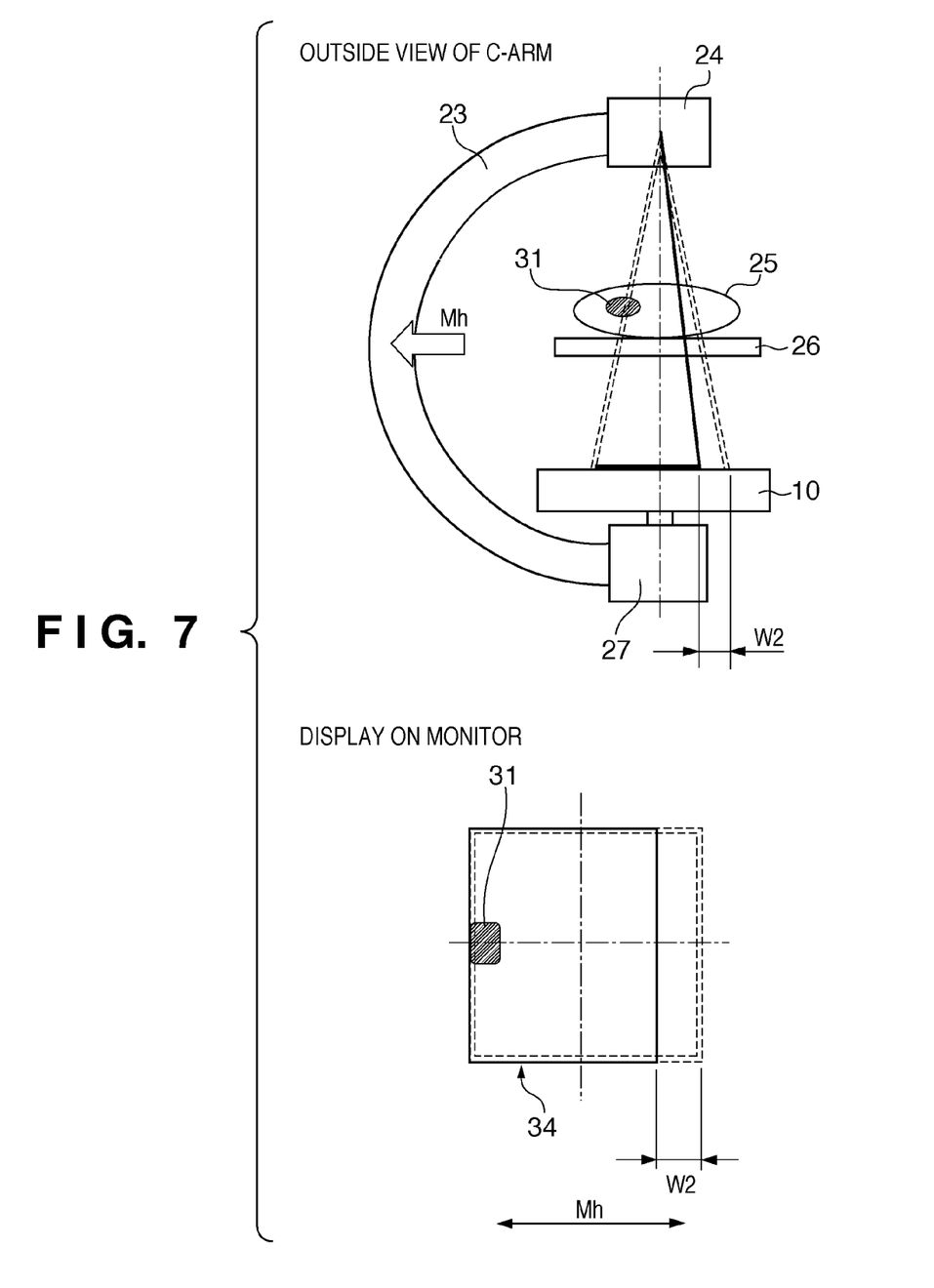
FIG. 7 is a view showing an example of the positional relationship between the C-arm 23 and the desired imaging target 31 and of the display form of the monitor.

For example, the above embodiment has exemplified a case in which, during positioning, an irradiated region on the moving direction side is enlarged in the direction in which the irradiated region is moving. However, the manner of changing the irradiated region during the positioning operation is not limited to this. For example, during the movement of the C-arm 23, it is possible to reduce the size of the irradiated region on the side opposite to the direction toward which the region is moving. More specifically, as shown in FIG. 7, an irradiated region on the right side corresponding to the direction side opposite to the moving direction of the C-arm 23 is reduced in the leftward direction by a width W2 as compared with normal operation. The purpose of this operation is to inhibit imaging of a region spaced apart from the desired imaging target 31 by regarding it as an unnecessary region. With this arrangement, it is possible to reduce X-ray irradiation of an unnecessary region during the positioning operation for a desired imaging target.

Figure 8:
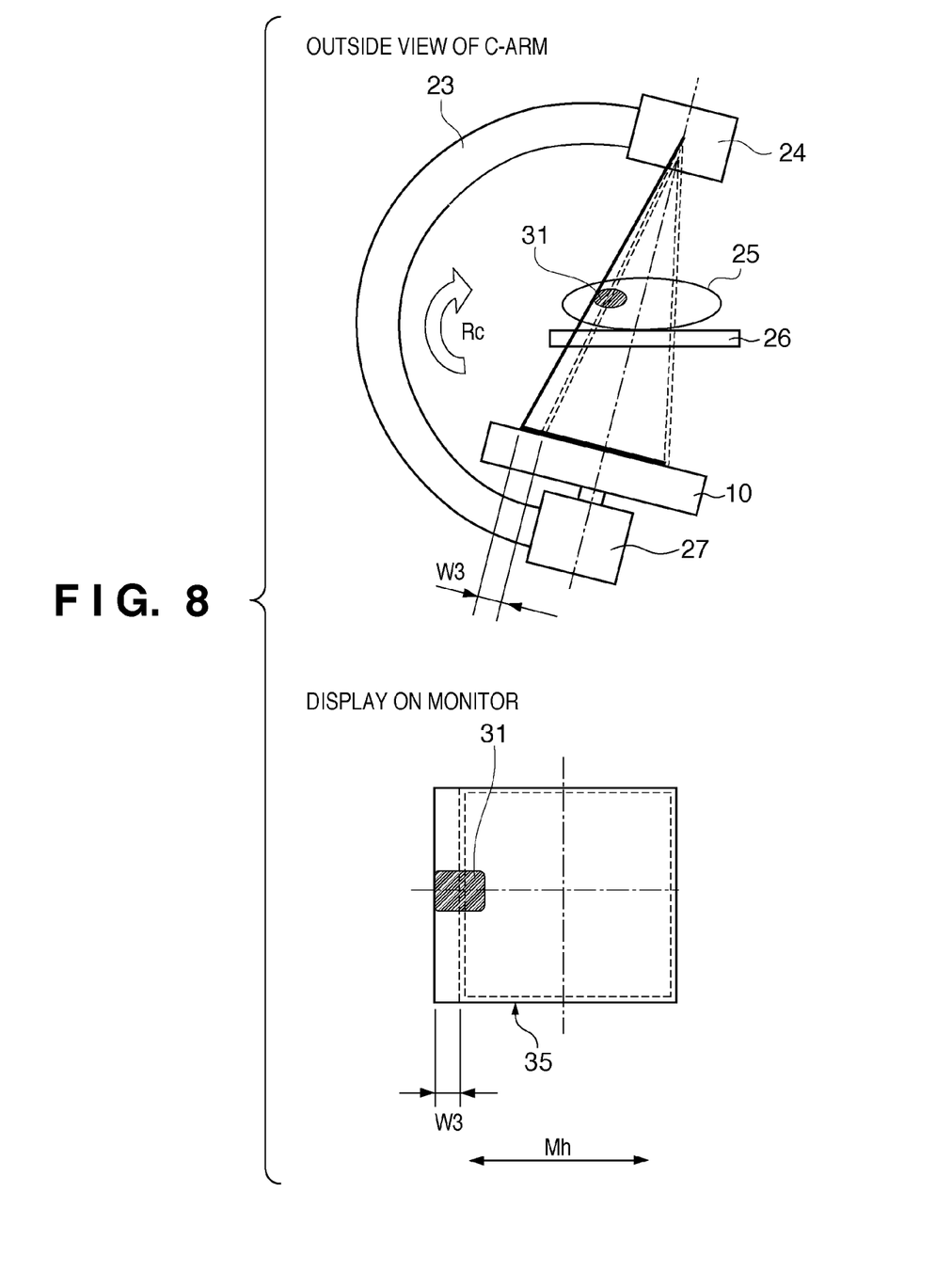
FIG. 8 is a view showing an example of the positional relationship between the C-arm 23 and the desired imaging target 31 and of the display form of the monitor.

In addition, the above embodiment has exemplified the case in which the irradiated region is changed in accordance with the movement of the C-arm 23. However, it is possible to change the irradiated region at the time of positioning operation in a fashion other than that described above. For example, it is possible to change the irradiated region in accordance with the rotation of the C-arm 23. More specifically, as shown in FIG. 8, when the C-arm 23 rotates in the Rc direction clockwise as shown, the irradiated region is changed in accordance with the rotation. In this case, during the rotation of the C-arm 23, the irradiated region on the left end is enlarged in the leftward direction by a width W3 as compared with its size in normal operation, in accordance with the movement of the irradiated region accompanying the rotation. In this arrangement, it is possible to change the irradiated region based on not only the position of the X-ray irradiation axis 27 relative to an object but also the relative angle.

Figure 9:
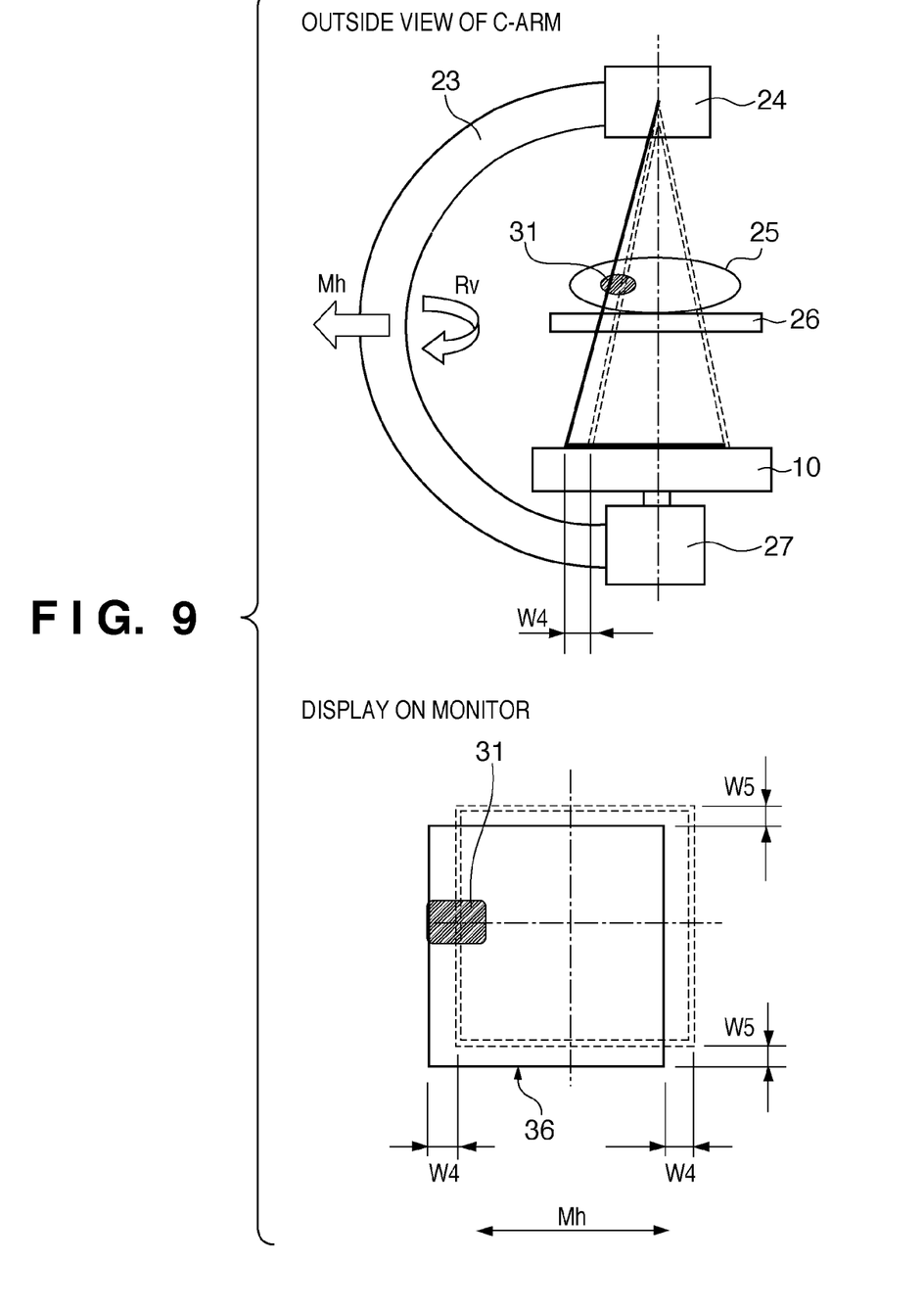
FIG. 9 is a view showing an example of the positional relationship between the C-arm 23 and the desired imaging target 31 and of the display form of the monitor.

Although the above embodiment has not referred to a case in which the C-arm 23 simultaneously moves or rotates in a plurality of directions, it is possible to change the irradiation direction in the above manner even when the C-arm 23 simultaneously moves or rotates in a plurality of directions. For example, an irradiated region can be changed in accordance with the movement or rotation of the C-arm 23. More specifically, as shown in FIG. 9, the above irradiated region changing operation is performed both when the C-arm 23 moves in the direction to move away from an object in the Mh direction and when the C-arm 23 rotates from the lower drawing surface side to the upper drawing surface side in the Rv direction. In this case, during the movement and rotation of the C-arm 23, an irradiated region on the left end is enlarged in the leftward direction by a width W4 as compared with that in normal operation in accordance with the movement of the irradiated region accompanying the movement of the C-arm 23, and an irradiated region on the lower end is enlarged in the downward direction by a width W6 as compared with that in normal operation in accordance with the movement of the irradiated region accompanying the rotation of the C-arm 23. In addition, in this case, an irradiated region on the direction side opposite to the moving direction and the rotating direction is reduced. More specifically, an irradiated region on the right end corresponding to the direction side opposite to the moving direction of the C-arm 23 is reduced in the leftward direction by the width W4 as compared with that in normal operation, and an irradiated region on the upper end corresponding to the direction side opposite to the rotating direction of the C-arm 23 is reduced in the downward direction by a width W6 as compared with that in normal operation. With this arrangement, it is possible to change an irradiated region based on the position and angle of the X-ray irradiation axis 27 relative to an object.

Although the above embodiment has not specifically referred to the moving speed or rotational speed of the C-arm 23, it is possible to provide speed detectors to detect these speeds and change an irradiated region in accordance with the detected speeds. Assume that the C-arm 23 moves at speeds V2 and V1 in the Mh direction, with V2>V1. Assume that in this case, an irradiated region is enlarged by a width W5 when the C-arm 23 moves at the moving speed V1, and an irradiated region is enlarged by a width W6 when the C-arm 23 moves at the moving speed V2. In this case, W5 and W6 have the relation represented by W6>W5. In this arrangement, it is possible to change the variation in the size of an imaging range in proportion to the moving speed or rotational speed of the C-arm. This improves the operability even when the imaging system is moved relative to an object at a high speed to greatly change the imaging range of the object.

The above embodiment has exemplified the X-ray imaging apparatus 20 of the type in which the top panel 26 which supports an object is fixed, and only the imaging system moves. However, the X-ray imaging apparatus to which the present invention is applied is not limited to this type of apparatus. The present invention can be applied to any X-ray imaging apparatus as long as it includes a detector to detect changes in relative position and angle between an imaging system and a top panel. For example, the present invention can be applied to a type of apparatus in which only the top panel moves or a type of apparatus in which both the imaging system and the top panel move. In addition, the imaging system or the top panel can be manually moved or motor-driven. Furthermore, the detector 29 may detect the movement or rotation of the C-arm 23 based on the analysis result obtained by analyzing changes between a plurality of continuously obtained images. In this case, a change in the relative position between the imaging system and an object is detected by computing information obtained by analysis.

According to the present invention, the operability at the time of positioning operation improves more than without this arrangement, thereby shortening the time required for positioning operation.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable storage medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-041300, filed Feb. 24, 2009, which is hereby incorporated by reference herein in its entirety.

What is claimed is:

1. A radiation imaging apparatus comprising:
   a radiation generator arranged to irradiate an object with radiation;
   a radiation detector arranged to detect radiation transmitted through the object;
   a detector arranged to detect at least one of movement and rotation of said radiation generator and said radiation detector; and
   a controller arranged to control said radiation generator to reduce a size of an irradiated region of the object on a side of a region opposite to a direction of movement of the irradiated region in accordance with at least one of the detected movement and the detected rotation.

2. The apparatus according to claim 1, wherein, when said detector detects at least one of the movement and the rotation, said controller is arranged to enlarge the size of the irradiated region of the object on the side of the region corresponding to the direction of movement of the irradiated region in accordance with the at least one of the detected movement and the detected rotation.

3. The apparatus according to claim 1, further comprising a speed detector arranged to detect at least one of moving speeds and rotational speeds of said radiation generator and said radiation detector relative to the object,
   wherein said controller is arranged to change a variation in a size of the irradiated region based on the at least one of the moving speed and the rotational speed detected by said speed detector.

4. The apparatus according to claim 1, wherein upon changing the irradiated region based on a detection result obtained by said detector, said controller is arranged to restore the changed irradiated region to an initial state when said detector cannot detect at least one of the movement and the rotation.

5. The apparatus according to claim 1, wherein said detector is arranged to analyze a change between a plurality of continuously obtained images based on detection by said radiation detector, and to detect at least one of the movement and the rotation based on the analysis result.

6. The apparatus according to claim 1, wherein
said radiation generator comprises an aperture mechanism arranged to adjust the amount of radiation, and
said controller is arranged to change the size of the irradiated region of the object by controlling said aperture mechanism.

7. The apparatus according to claim 1, further comprising:
a supporting unit arranged to support said radiation generator and said radiation detector while keeping the distance therebetween constant;
an object supporting unit positioned between said radiation generator and said radiation detector and arranged to support the object; and
a moving unit arranged to move said supporting unit relative to the object.

8. A processing method in a radiation imaging apparatus which obtains a radiographic image, the method comprising:
causing a radiation generator to irradiate an object with radiation;
causing a radiation detector to detect radiation transmitted through the object;
detecting at least one of movement and rotation of the radiation generator and the radiation detector; and
controlling the radiation generator to reduce a size of an irradiated region of the object on a side of a region opposite to a direction of movement of the irradiated region in accordance with at least one of the detected movement and the detected rotation.

9. A radiation generator control apparatus comprising:
a detector arranged to detect at least one of movement and rotation of a radiation generator arranged to irradiate an object with radiation and a radiation detector arranged to detect radiation transmitted through the object; and
a controller arranged to control the radiation generator to reduce a size of an irradiated region of the object on a side of a region opposite to a direction of movement of the irradiated region in accordance with at least one of the detected movement and the detected rotation.

* * * * *